US009133484B2

(12) United States Patent
Yoshida et al.

(10) Patent No.: US 9,133,484 B2
(45) Date of Patent: Sep. 15, 2015

(54) TRANSFECTION AGENT

(75) Inventors: Daizo Yoshida, Tokyo (JP); Jiro Takei, Tokyo (JP)

(73) Assignees: 3-D MATRIX, LTD., Tokyo (JP); NIPPON MEDICAL SCHOOL FOUNDATION, Tokyo (JP)

( * ) Notice: Subject to any disclaimer, the term of this patent is extended or adjusted under 35 U.S.C. 154(b) by 758 days.

(21) Appl. No.: 13/058,880

(22) PCT Filed: Aug. 26, 2009

(86) PCT No.: PCT/JP2009/064814
§ 371 (c)(1),
(2), (4) Date: Feb. 14, 2011

(87) PCT Pub. No.: WO2010/024262
PCT Pub. Date: Mar. 4, 2010

(65) Prior Publication Data
US 2011/0152203 A1 Jun. 23, 2011

(30) Foreign Application Priority Data
Aug. 27, 2008 (JP) ................................. 2008-217958

(51) Int. Cl.
*C07K 7/06* (2006.01)
*C12N 15/87* (2006.01)
*B82Y 5/00* (2011.01)
*A61K 47/42* (2006.01)

(52) U.S. Cl.
CPC . *C12N 15/87* (2013.01); *B82Y 5/00* (2013.01); *C07K 7/06* (2013.01); *A61K 47/42* (2013.01)

(58) Field of Classification Search
CPC ........................................................ C07K 7/06
See application file for complete search history.

(56) References Cited

U.S. PATENT DOCUMENTS

2003/0176335 A1* 9/2003 Zhang et al. .................... 514/12
2009/0156427 A1* 6/2009 Zhang et al. .................... 506/12

FOREIGN PATENT DOCUMENTS

| JP | 2001-517939 A | 10/2001 |
| WO | WO 96/40961 A1 | 12/1996 |
| WO | WO 03/006043 A1 | 1/2003 |

OTHER PUBLICATIONS

Zhang et al., 2006, siRNA-containing liposomes modified with polyarginine effectively silence the targeted gene, Journal of Controlled Release, 112: 229-239.*
Vauthey et al., 2002, Molecular self-assembly of surfactant-like peptides to form nanotubes and nanovesicles, PNAS, 99(8): 5355-5360.*
von Maltzahn et al., 2003, Positively Charged Surfactant-like Peptides Self-assemble into Nanostructures, Langmuir, 19: 4332-4337.*
Noguchi et al., 2006, Protein Transduction Technology: A Novel Therapeutic Perspective, Acta Med. Okayama, 60(1): 1-11.*
Belkaid et al., 2007, Necrosis Induction in Glioblastoma Cells Reveals a New "Bioswitch" Function for the MT1-MMP/G6PT Signaling Axis in proMMP-2 Activation versus Cell Death Decision, Neoplasia, 9(4): 332-340.*
Dai et al., 2007, Aberrant FoxM1B expression increases matrix metalloproteinase-2 transcription and enhances the invasion of glioma cells, Oncogene, 26: 6212-6219.*
Zhang et al., 2005, The chemokine stromal cell derived factor-1 (CXCL12) promotes glioma invasiveness through MT2-matrix metalloproteinase, Carcinogenesis, 26(12): 2069-2077.*
Kargiotis et al., 2008, Adenovirus-mediated Transfer of siRNA Against MMP-2 mRNA Results in Impaired Invasion and Tumor-Induced Angiogenesis, Induces Apoptosis in vitro and inhibits Tumor Growth in vivo in Glioblastoma.*
International Search Report, dated Sep. 29, 2009 issued in PCT/JP2009/064814.
Nagai et al., "Dynamic Behaviors of Lipid-Like Self-Assembling Peptide A6D and A6K Nanotubes", Journal of Nanoscience and Nanotechnology, vol. 7, 2007, pp. 2246-2252.
Yaghmur et al., "Tuning Curvature and Stability of Monoolein Bilayers by Designer Lipid-Like Peptide Surfactants", PLoS ONE, vol. 2, Issue 5, e479, May 2007, pp. 1-10.
Yeh et al., "Peptergents: Peptide Detergents That Improve Stability and Functionality of a Membrane Protein, Glycerol-3-phosphate Dehydrogenase, Biochemistry", vol. 44, No. 51, 2005, pp. 16912-16919.
Zhao et al., "Designer Self-Assembling Peptide Materials", Marcomolecular Bioscience, vol. 7, Jan. 2007, pp. 13-22.
Zhao et al., "Designer short peptide surfactants stabilize G protein-coupled receptor bovine rhodopsin", Proc. Natl. Acad. Sci. USA, vol. 103, No. 47, Nov. 21, 2006, pp. 17707-17712.
Zhao et al., "Self-Assembling Nanopeptides Become a New Type of Biomaterial", Adv Polym Sci, vol. 203, 2006, pp. 145-170.
Santoso et al. "Self-assembly of Surfactant-like Peptides with Variable Glycine Tails to Form Nanotubes and Nanovesicles", Nano Letters, vol. 2, No. 7, p. 687-691, 2002.
Stevenson et al., "Delivery of siRNA by histidine-containing reducible polycations", Journal of Controlled Release, vol. 130., p. 46-56, 2008.
Supplementary European Search Report dated Feb. 10, 2012, for Application No. 09809913.
Von Maltzahn et al., "Positively Charged Surfactant-like Peptides Self-assemble into Nanostuctures", Langmuir, vol. 19, 2003, p. 4332-4337.
Wang et al., "An intracellular delivery method for siRNA by an arginine-rich peptide", J. Biochem. Biophys. Methods, vol. 70, 2007, p. 579-586.
European Summons to attend oral proceedings pursuant to Rule 115(1) EPC dated Jun. 26, 2013 for European Application No. 09809913.8.
Zhang, "Building from the bottom up," Materials Today, vol. 6, Issue 5, May 2003, pp. 20-27, XP055063929.
Zhao et al., "Fabrication of molecular materials using peptide construction motifs," Trends in Biotechnology, vol. 22, Issue 9, Sep. 2004, pp. 470-476, XP004552612.

* cited by examiner

*Primary Examiner* — Amber D Steele
(74) *Attorney, Agent, or Firm* — Birch, Stewart, Kolasch & Birch, LLP (57) ABSTRACT

A transfection agent is provided that has lower toxicity and can be applied in the clinical setting. The transfection agent comprises a peptide surfactant.

2 Claims, 5 Drawing Sheets

TRANSFECTION AGENT

TECHNICAL FIELD

The present invention relates to a transfection agent that contains a peptide surfactant.

BACKGROUND ART

RNA interference (RNAi) is expected to be applied to the treatment of disease since it is able to inhibit the expression of specific genes. At the current level of technology, transfection agents used when transfecting cells with small interfering RNA (siRNA) consist mainly of cationic phospholipids that have been indicated to be toxic.

However, when considering the application of siRNA and other nucleic acid pharmaceuticals in the clinical setting, transfection agents are desired to have as low toxicity as possible, and the development of a transfection agent having lower toxicity has been awaited.

Peptide surfactants are known to have an action that stabilizes membrane proteins such as the G protein coupled receptor, bovine rhodopsin, and be capable of self-assembly (Non-Patent Documents 1 and 2). However, their application as transfection agents has heretofore been unknown.

Non-Patent Document 1: Zhao, X. et al., PNAS, Vol. 103, No. 47, 17707-17712

Non-Patent Document 2: Nagai, A., et al., J. Nanosci. Nanotechnol., Vol. 7, No. 7, 1-7

DISCLOSURE OF THE INVENTION

Problems to be Solved by the Invention

An object of the present invention is to provide a transfection agent that has lower toxicity and can be applied in the clinical setting.

As a result of conducting extensive studies to solve the aforementioned problems, the inventors of the present invention found that a peptide surfactant is useful as a transfection agent, thereby leading to completion of the present invention.

Thus, the present invention relates to the following:
1. a transfection agent comprising a peptide surfactant;
2. the transfection agent described in 1 above, wherein the peptide surfactant consists of a head portion consisting of 4 to 10 hydrophilic amino acids and a tail portion consisting of 1 or 2 hydrophobic amino acids;
3. the transfection agent described in 1 above, wherein the peptide surfactant is AAAAAAD (SEQ ID NO: 5)or AAAAAAK(SEQ ID NO:7); and,
4. a pharmaceutical comprising the transfection agent described in any of 1 to 3 above and nucleic acid.

In the present invention, a peptide surfactant refers to that which contains 6 to 10 amino acid residues, has a length of about 2 to 3 nm, and demonstrates properties similar to those of conventional surfactants such as n-dodecyl-β-D-maltoside (DM) or octyl-D-glucoside (OG).

The peptide surfactant of the present invention is preferably consists of a head portion consisting of 4 to 10 hydrophilic amino acids and a tail portion consisting of 1 or 2 hydrophobic amino acids.

More specifically, although examples of peptide surfactants that can be used include GGGGDD (G4D2)(SEQ ID NO: 1), GGGGGGDD (G6D2)(SEQ ID NO: 2), GGGGGGGGDD (G8D2)(SEQ ID NO: 3), GGGGGGGGGGDD (G10D2) (SEQ ID NO: 4), AAAAAAD (A6D)(SEQ ID NO: 5), AAAAAADD (A6D2) (SEQ ID NO: 6), AAAAAAK (A6K)(SEQ ID NO: 7), AAAAAAKK (A6K2) (SEQ ID NO: 8), VVVVVVD (V6D) (SEQ ID NO: 9), VVVVVVDD (V6D2)(SEQ ID NO: 10), VVVVVVK (V6K)(SEQ ID NO: 11), VVVVVVKK (V6K2) (SEQ ID NO:12), LLLLLLD (L6D)(SEQ ID NO:13), LLLLLLDD (L6D2)(SEQ ID NO: 14), LLLLLLK (L6K) (SEQ ID NO: 15) and LLLLLLKK (L6K2)(SEQ ID NO: 16), AAAAAAD (A6D)(SEQ ID NO: 5) and AAAAAAK (A6K) (SEQ ID NO: 7) are preferable, while AAAAAAK (A6K) (SEQ ID NO: 7) is particularly preferable.

The peptide surfactant of the present invention can be produced using a conventionally known solid-phase synthesis method. In addition, peptides artificially synthesized in this manner can be used preferably since they do not contain substances of biological origin and are free of risk of infection.

In the present invention, a transfection agent refers to a composition used for introducing a polynucleotide or gene such as siRNA into cells, that is capable of enhancing the transfection efficiency thereof.

The transfection agent of the present invention can be incorporated into pharmaceuticals with a desired nucleic acid. In addition, the pharmaceuticals of the present invention can be used for oral administration or parenteral administration.

A nucleic acid used in the pharmaceutical of the present invention uses a portion of a gene base sequence targeted for use in treatment either as is or after modifying, is composed of DNA or RNA nucleic acid, and is able to regulate the function of a desired gene in the body. Such nucleic acids are typically referred to as nucleic acid medicines.

Examples of nucleic acid medicines include decoy nucleic acid medicines that inhibit gene expression by causing a transcription regulatory factor to bind to an oligonucleotide having the same sequence as a constant region (cis element) of intranuclear DNA bound by the transcription regulatory factor, nucleic acid aptamers capable of specifically binding with specific molecules, ribozymes having catalytic activity that cleaves RNA, antisense RNA that inhibits gene expression by complementarily binding to a specific region of a target gene mRNA, and siRNA that decomposes mRNA by binding to a specific region of mRNA of a target gene along with an RNA-induced silencing complex. Decoy nucleic acid medicines, nucleic acid aptamers and ribozymes are nucleic acids that adopt a sophisticated, specific three-dimensional structure, antisense RNA is a single-stranded RNA oligomer having a sequence on the side of the opposite strand of a portion of an mRNA sequence, and siRNA is a short double-stranded RNA that has the same sequence as a portion of the mRNA of a target gene. These nucleic acids can be produced artificially by chemical reactions using a nucleic acid synthesizer, or can be produced in cultured cells using a vector.

Although previous pharmaceuticals were mainly of low molecular weight compounds, biopharmaceuticals composed of chemical substances present in the body are currently attracting attention due to their target specificity and biological safety. Nucleic acid medicines are included in these biopharmaceuticals, and are currently being developed by numerous research institutes and pharmaceutical corporations. Among these nucleic acid medicines, attention has recently been focused on the specific gene inhibitory effects of siRNA in particular, and siRNA pharmaceuticals are being developed for various diseases. Treatment of glioblastoma, which is a type of brain tumor, is one example of a disease for which the use of siRNA is expected to demonstrate therapeutic effects. In glioblastoma, apoptosis is induced in tumor cells by RNAi targeted at MMP-2, and is known to be effective in inhibiting tumor growth.

Examples of pharmaceutical forms include tablets, capsules, granules and syrups. These pharmaceuticals can be produced by using additives ordinarily used in the production of pharmaceuticals.

Although there are no particular limitations on the dosage of the pharmaceutical of the present invention, it is, for example, 0.001 to 10 mg/kg of body weight per day in the case of parenteral administration. This dosage can be administered once per day or divided among two to three administrations per day, and can be suitably adjusted according to age, pathology and symptoms.

Specific examples of additives include lactose, dextrin, sucrose, mannitol, cornstarch, sorbitol, microcrystalline cellulose and polyvinyl pyrrolidone. These can be used alone or in a suitable combination thereof. These pharmaceuticals can be produced using a method suitable for the form of each pharmaceutical in accordance with methods described in the Japanese Pharmacopeia. In addition, flavoring agents, colorants or sweeteners and the like can also be suitably used. The contents of these additives can be suitably selected by a person with ordinary skill in the art.

Examples of the forms of quasi drugs include tablets, capsules, granules, jellies and drinks. These quasi drugs can be produced using additives ordinarily used in the production of quasi drugs. Moreover, these quasi drugs can also contain other active ingredients such as vitamins. In addition, additives such as sweeteners, flavoring agents, colorants or antioxidants can be used alone or in a suitable combination thereof. These quasi drugs can be produced using methods known among persons with ordinary skill in the art.

EXAMPLE 1

Comparison of Cytotoxicity of Peptide Surfactant and Cationic Liposome-Mediated Gene Transfer Agents Cytotoxicity was evaluated using cultured human cells for a peptide surfactant and two types of currently widely used cationic liposome-mediated gene transfer agents.

<Materials>
*Added Substances
1. Peptide surfactant (sequence: Ac-AAAAAAK-NH$_2$ (SEQ ID NO: 17), Celtek)
2. Lipofectamine 2000 (Invitrogen)
3. siFECTOR (B-Bridge International, Inc.)
*Cells
Cultured human malignant glioma cells (U87MG, acquired from ATCC)
*MTT Assay Reagent (for cell proliferation assay)
Cell Titer 96 Aqueous One Solution Cell Proliferation Assay Kit (Promega)
<Method>
The cells were seeded in a 96-well plate in accordance with the recommended ATCC protocol (cell density: $2 \times 10^4$/well) followed by incubating overnight. The medium was replaced with fresh medium and the substances were added (final concentrations: 0.0005, 0.001, 0.005, 0.01, 0.05, 0.1, 0.5, 1, 5, 10, 25, 50, 75, 100, 250 and 500 µg/ml). The cells were cultured for 24 hours. After culturing, Cell Titer 96 Aqueous One Solution was added (20 µl/well) followed by measuring optical absorbance at 495 nm with a plate reader 4 hours later to quantify the number of viable cells.

Figure 1:
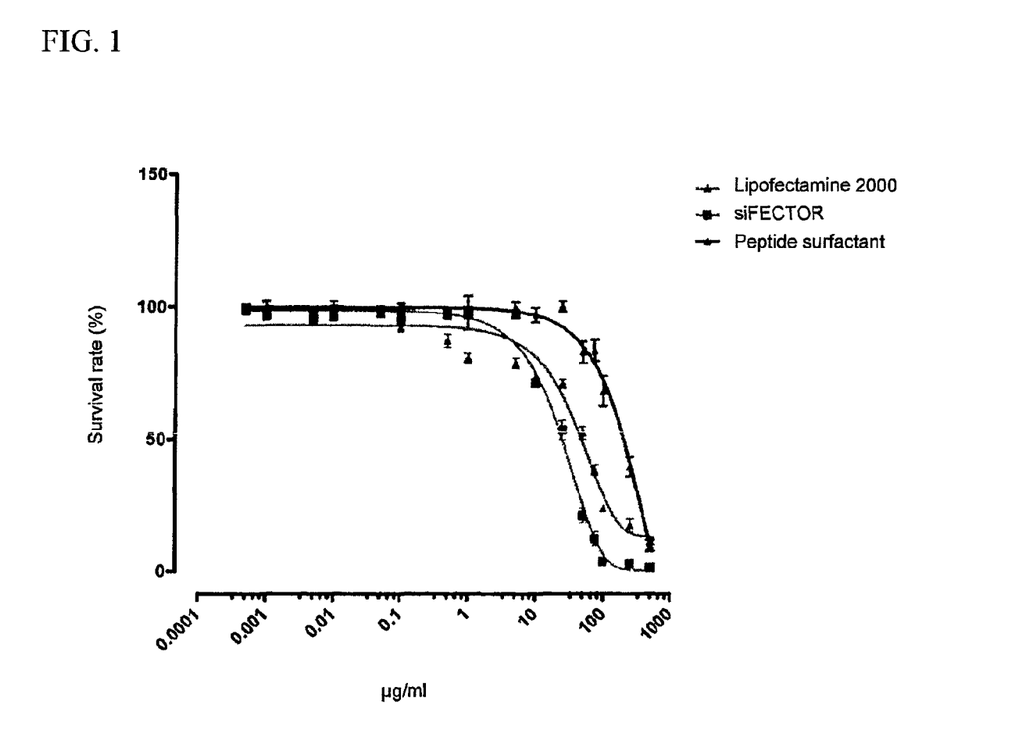
FIG. 1 is a graph indicating a comparison of cytotoxicity between a peptide surfactant and cationic liposome-mediated gene transfer agents (Lipofectamine 2000 and siFECTOR).

As is clear from FIG. 1, the peptide surfactant demonstrated the lowest level of toxicity. LD50 values were 285.9 µg/ml for the peptide surfactant, 42.49 µg/ml for Lipofectamine 2000, and 25.3 µg/ml for siFECTOR. The peptide surfactant did not demonstrate cytotoxicity at concentrations of 25 µg/ml or less.

EXAMPLE 2

Confirmation of Introduction of siRNA into Cells by Peptide Surfactant

The introduction of siRNA into cells by peptide surfactant was confirmed by microscopic observation of fluorescent-labeled siRNA.

<Materials>
*Peptide surfactant
Sequence: Ac-AAAAAAK-NH$_2$ (SEQ ID NO: 17) (Celtek)
*siRNA
siRNA/MMP-2 (Santa Cruz)
*siRNA fluorescent labeling reagent
Label IT Cy-3 Labeling Kit (Mirus)
*Cells
Three types of cultured human malignant glioma cells (U87MG, T98G, U251MG, each acquired from ATCC)
<Method>
siRNA/MMP-2 was labeled with Cy3 using the siRNA fluorescent labeling reagent in accordance with the Mirus protocol. 5000 of the cells were seeded into a chambered slide glass in accordance with the ATCC protocol and incubated for overnight. After removing the medium, siRNA to a final concentration of 50 nM and peptide surfactant to a final concentration of 20 µg/ml were added to 1 ml of medium followed by culturing for 8 hours. In a control group, only siRNA was cultured at a final concentration of 50 nM in 1 ml of medium. The cells were observed with an inverted fluorescence microscope by fluorescent observation with a Cy3 filter and by bright field observation.

<Results>
Uptake of the Cy3-labeled siRNA was confirmed in the test group to which both peptide surfactant and siRNA were added for all three types of cells. Uptake of labeled siRNA was not observed for any of the cells in the control group to which only siRNA was added.

EXAMPLE 3

Analysis of Time-Based Changes in Amount of siRNA Introduced into Cells by Peptide Surfactant Time-based changes in the amounts of siRNA introduced into cells by peptide surfactant were examined by microscopic observation of fluorescent-labeled siRNA.
<Materials>
*Peptide surfactant
Sequence: Ac-AAAAAAK-NH$_2$ (SEQ ID NO: 17) (Celtek)
*Peptide surfactant concentrations:
0, 0.5, 1.0, 5.0, 10.0, 20.0, 25.0 μg/ml
*siRNA
siRNA/MMP-2 (Santa Cruz)
siRNA fluorescent labeling reagent
Label IT Cy-3 Labeling Kit (Mirus)
*Cells
Three types of cultured human malignant glioma cells (U87MG, T98G, U251MG, acquired from ATCC)
<Method>
siRNA/MMP-2 was labeled with Cy3 using the siRNA fluorescent labeling reagent in accordance with the Minis standard protocol. The labeled siRNA was then mixed with the peptide surfactant. siRNA to a final concentration of 50 nM and peptide surfactant to a final concentration of 20 μg/ml were administered to $1 \times 10^5$ cells seeded in a 24-well plate containing medium at 1 ml/well, followed by incubating for 0.5, 1, 2, 4, 8, 16 and 24 hours. After washing the wells with PBS, the cells were recovered and transferred to a 96-well plate where they were measured for optical absorbance.

Figure 2:
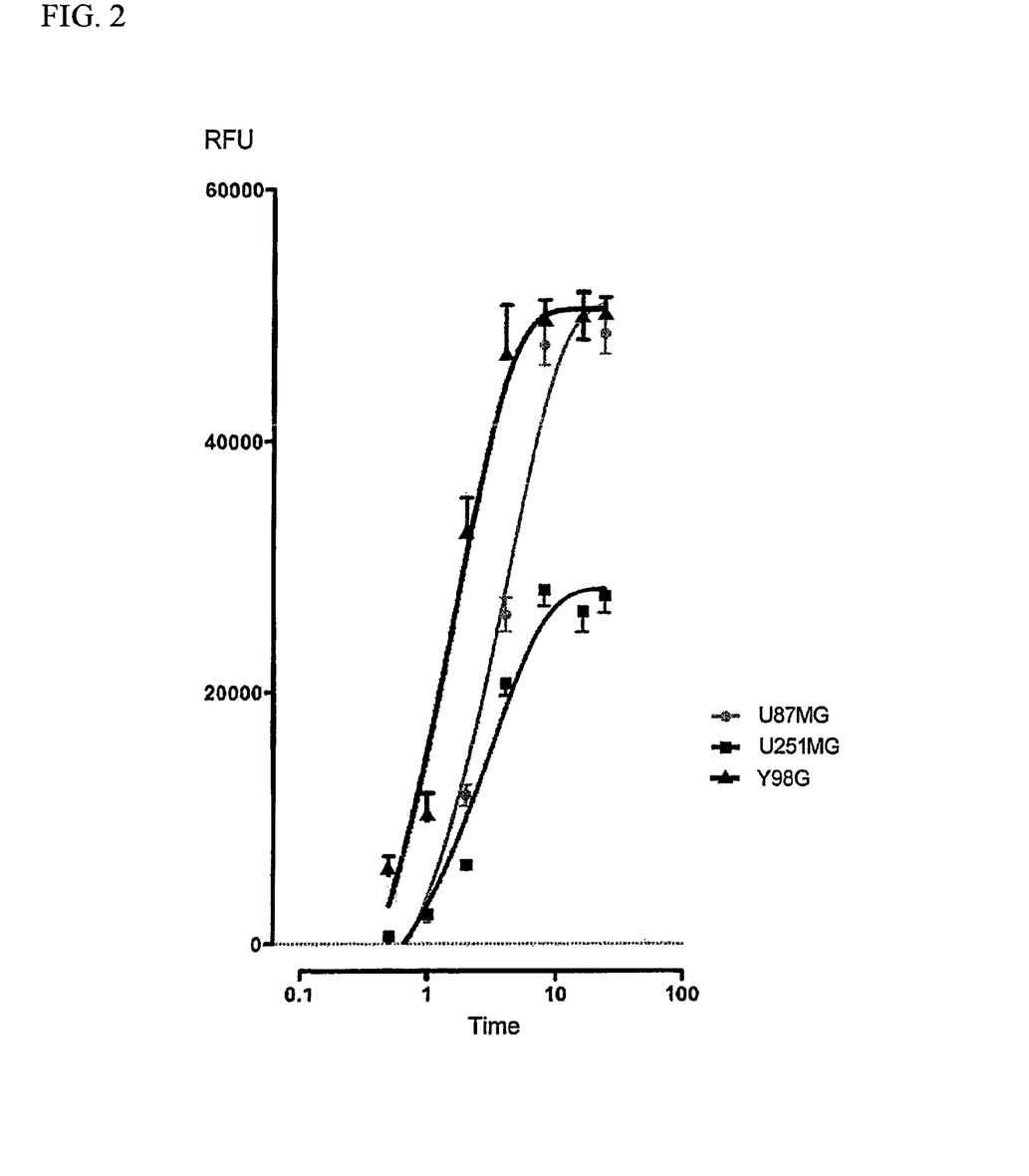
FIG. 2 is a graph indicating the results of an analysis of time-based changes in the amount of siRNA introduced into three types of cultured human malignant glioma cells using a peptide surfactant.

The results are shown in FIG. 2.
During culturing for 1 to 8 hours, relative fluorescence units (RFU) increased nearly proportionately, and siRNA was determined to be incorporated into the cells in proportion to time.
During culturing for longer than 8 hours, RFU levels essentially reached a plateau.

EXAMPLE 4

Analysis of Relationship between Peptide Surfactant Concentration and siRNA Introduction Efficiency The manner in which the efficiency of introduction of siRNA into cells is dependent on concentration of peptide surfactant was examined by microscopic observation of fluorescent-labeled siRNA.
<Materials>
*Peptide surfactant
Sequence: Ac-AAAAAAK-NH$_2$ (SEQ ID NO: 17) (Celtek)
*Peptide surfactant concentrations:
0, 0.5, 1.0, 5.0, 10.0, 20.0, 25.0 μg/ml
*siRNA
siRNA/MMP-2 (Santa Cruz)
*siRNA fluorescent labeling reagent
Label IT Cy-3 Labeling Kit (Mirus)
*Cells
Three types of cultured human malignant glioma cells (U87MG, T98G, U251MG, acquired from ATCC)
<Method>
siRNA/MMP-2 was labeled with Cy3 using the siRNA fluorescent labeling reagent in accordance with the Minis standard protocol. The labeled siRNA was then mixed with the peptide surfactant. siRNA to a final concentration of 50 nM and peptide surfactant to final concentrations of 0, 0.5, 1, 5, 10, 20 and 25 μg/ml were administered to $1 \times 10^5$ cells seeded in a 24-well plate containing medium at 1 ml/well, followed by culturing for 8 hours. After washing the wells with PBS, the cells were recovered and transferred to a 96-well plate where they were measured for optical absorbance.

Figure 3:
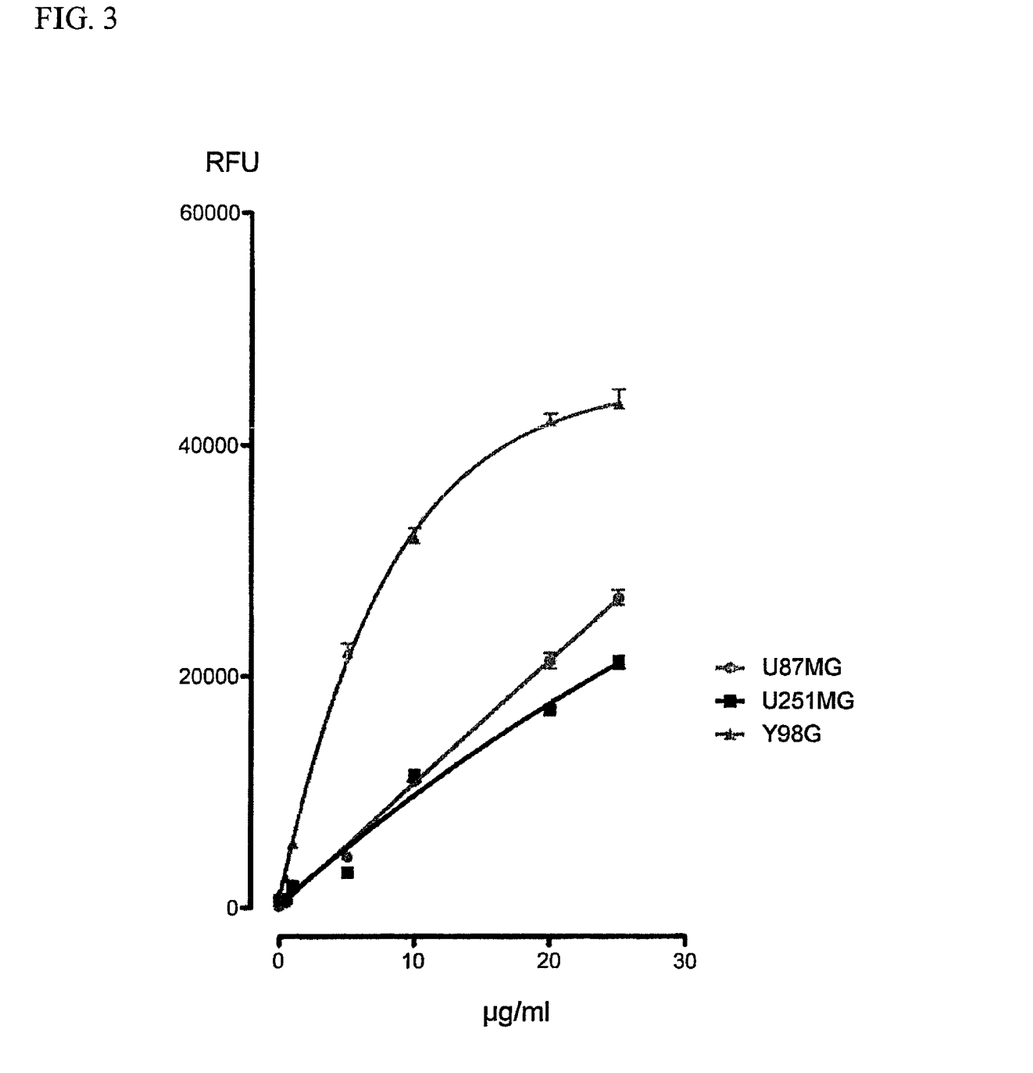
FIG. 3 is a graph indicating the results of an analysis of the relationship between peptide surfactant concentration and siRNA introduction efficiency.

The results are shown in FIG. 3.
Although dose-dependent increases in RFU weakened at 10 μg/ml and above in the Y98G cells, increases in RFU in proportion to increases in concentration were observed for all three cell types, and introduction of siRNA into cells was clearly determined to be dependent on peptide surfactant concentration.
When considering together with the results of Example 3, exposing cells to peptide surfactant at a concentration of 20 μg/ml for 8 hours was clearly determined to adequately and significantly result in introduction of siRNA into cells.

EXAMPLE 5

Confirmation of Effects of RNA Interference by siRNA Introduced into Cells Using Peptide Surfactant siRNA introduced into cells by peptide surfactant was confirmed to have RNA interference ability by RT-PCR.
<Materials>
*Peptide surfactant
Sequence: Ac-AAAAAAK-NH$_2$ (SEQ ID NO: 17) (Celtek)
*Cells
Three types of cultured human malignant glioma cells (U87MG, T98G, U251MG, acquired from ATCC)
<Method>
$1 \times 10^5$ cells were seeded into a 24-well plate and cultured overnight in accordance with the ATCC standard protocol. After removing the medium, the following solutions were added to the final concentrations indicated below followed by culturing for 8 hours under the same culturing conditions as previously described.
(1) Blank control (medium only)
(2) Random oligo siRNA (Dharmacon)/peptide surfactant 20 μg/ml
(3) siRNA 50 nM
(4) Peptide surfactant 20 μg/ml
(5) siRNA 50 nM/peptide surfactant 20 μg/ml The siRNA was reverse-transcribed to cDNA using the Taqman Gene Expression Cell-to-Ct Kit (Applied Biosystems). Quantitative analysis was carried out using the Applied Biosystems 7500 Real-Time PCR System using MMP-2 for the target and beta-actin for the internal standard by Gene Expression Assay (Applied Biosystems).

Figure 4:
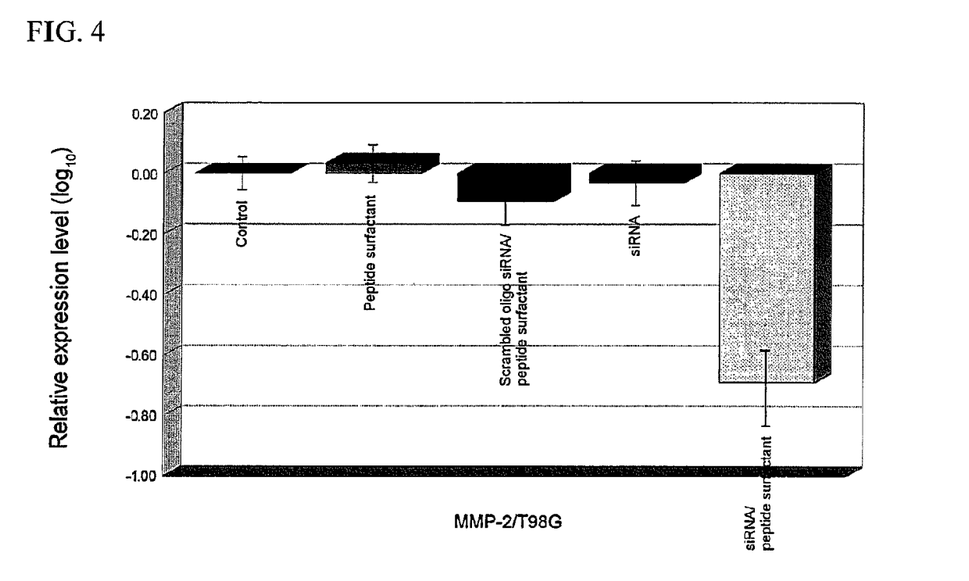
FIG. 4 is a graph indicating the results of confirming RNA interference effects by siRNA introduced into three types of cultured human malignant glioma cells by peptide surfactant.
Figure 5:
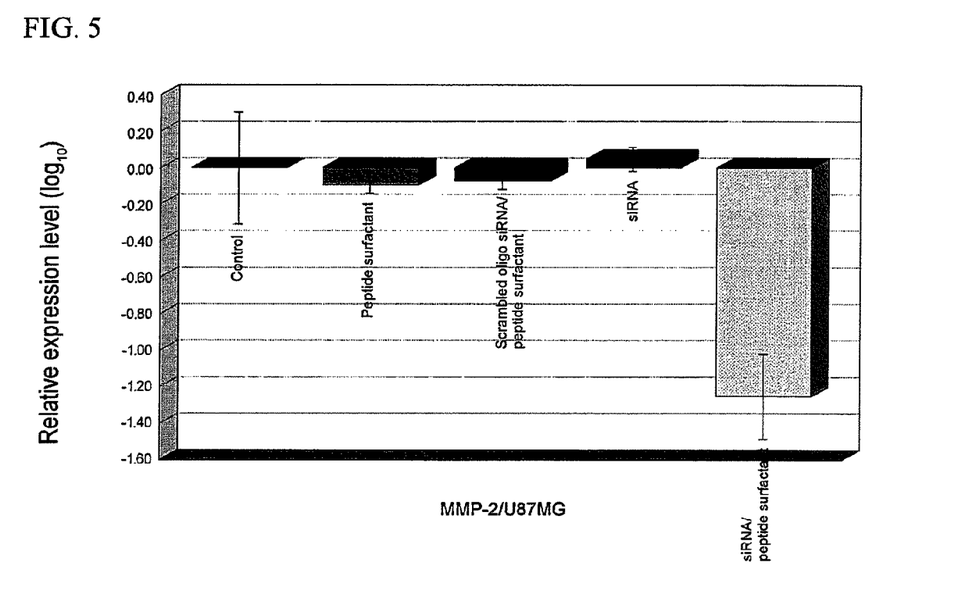
FIG. 5 is a graph indicating the results of confirming RNA interference effects by siRNA introduced into three types of cultured human malignant glioma cells by peptide surfactant.
Figure 6:
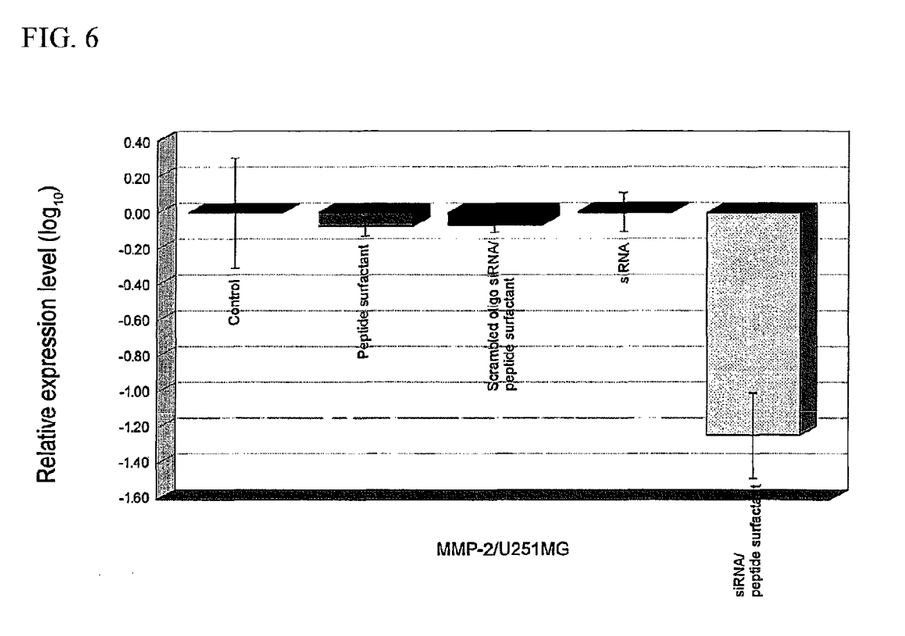
FIG. 6 is a graph indicating the results of confirming RNA interference effects by siRNA introduced into three types of cultured human malignant glioma cells by peptide surfactant.

The results are shown in FIGS. 4 to 6.
Expression of MMP-2 mRNA was significantly inhibited only in the case of administration of siRNA 50 nM/peptide surfactant 20 μg/ml.
Since effects on introduction into cells are not present in the case of siRNA only, siRNA is believed to be incorporated into cells due to an siRNA introduction effect of peptide surfactant, thereby resulting in RNA interference effects.

Since inhibition of MMP-2 gene was not observed in the case of mixing peptide surfactant with random oligo RNA, which is composed of a sequence for which homology is not observed in the human genome and which is not gene-specific, the reaction was considered as not being a non-specific reaction which is independent of the RNA sequence.

The invention claimed is:

1. A method for treating a tumor, comprising:
   administering a pharmaceutical composition comprising SEQ ID NO: 7 and an isolated or artificial siRNA to a subject.

2. The method for treating according to claim 1, wherein the tumor is brain tumor.

* * * * *

SEQUENCE LISTING

```
<160> NUMBER OF SEQ ID NOS: 17

<210> SEQ ID NO 1
<211> LENGTH: 6
<212> TYPE: PRT
<213> ORGANISM: Artificial Sequence
<220> FEATURE:
<223> OTHER INFORMATION: synthesized peptide

<400> SEQUENCE: 1

Gly Gly Gly Gly Asp Asp
1               5

<210> SEQ ID NO 2
<211> LENGTH: 8
<212> TYPE: PRT
<213> ORGANISM: Artificial Sequence
<220> FEATURE:
<223> OTHER INFORMATION: synthesized peptide

<400> SEQUENCE: 2

Gly Gly Gly Gly Gly Gly Asp Asp
1               5

<210> SEQ ID NO 3
<211> LENGTH: 10
<212> TYPE: PRT
<213> ORGANISM: Artificial Sequence
<220> FEATURE:
<223> OTHER INFORMATION: synthesized peptide

<400> SEQUENCE: 3

Gly Gly Gly Gly Gly Gly Gly Gly Asp Asp
1               5                   10

<210> SEQ ID NO 4
<211> LENGTH: 12
<212> TYPE: PRT
<213> ORGANISM: Artificial Sequence
<220> FEATURE:
<223> OTHER INFORMATION: synthesized peptide

<400> SEQUENCE: 4

Gly Gly Gly Gly Gly Gly Gly Gly Gly Gly Asp Asp
1               5                   10

<210> SEQ ID NO 5
<211> LENGTH: 7
<212> TYPE: PRT
<213> ORGANISM: Artificial Sequence
<220> FEATURE:
<223> OTHER INFORMATION: synthesized peptide

<400> SEQUENCE: 5

Ala Ala Ala Ala Ala Ala Asp
1               5

<210> SEQ ID NO 6
<211> LENGTH: 8
<212> TYPE: PRT
<213> ORGANISM: Artificial Sequence
```

```
<220> FEATURE:
<223> OTHER INFORMATION: synthesized peptide

<400> SEQUENCE: 6

Ala Ala Ala Ala Ala Ala Asp Asp
1               5

<210> SEQ ID NO 7
<211> LENGTH: 7
<212> TYPE: PRT
<213> ORGANISM: Artificial Sequence
<220> FEATURE:
<223> OTHER INFORMATION: synthesized peptide

<400> SEQUENCE: 7

Ala Ala Ala Ala Ala Ala Lys
1               5

<210> SEQ ID NO 8
<211> LENGTH: 8
<212> TYPE: PRT
<213> ORGANISM: Artificial Sequence
<220> FEATURE:
<223> OTHER INFORMATION: synthesized peptide

<400> SEQUENCE: 8

Ala Ala Ala Ala Ala Ala Lys Lys
1               5

<210> SEQ ID NO 9
<211> LENGTH: 7
<212> TYPE: PRT
<213> ORGANISM: Artificial Sequence
<220> FEATURE:
<223> OTHER INFORMATION: synthesized peptide

<400> SEQUENCE: 9

Val Val Val Val Val Val Asp
1               5

<210> SEQ ID NO 10
<211> LENGTH: 8
<212> TYPE: PRT
<213> ORGANISM: Artificial Sequence
<220> FEATURE:
<223> OTHER INFORMATION: synthesized peptide

<400> SEQUENCE: 10

Val Val Val Val Val Val Asp Asp
1               5

<210> SEQ ID NO 11
<211> LENGTH: 7
<212> TYPE: PRT
<213> ORGANISM: Artificial Sequence
<220> FEATURE:
<223> OTHER INFORMATION: synthesized peptide

<400> SEQUENCE: 11

Val Val Val Val Val Val Lys
1               5

<210> SEQ ID NO 12
<211> LENGTH: 8
<212> TYPE: PRT
<213> ORGANISM: Artificial Sequence
```

```
<220> FEATURE:
<223> OTHER INFORMATION: synthesized peptide

<400> SEQUENCE: 12

Val Val Val Val Val Val Lys Lys
1               5

<210> SEQ ID NO 13
<211> LENGTH: 7
<212> TYPE: PRT
<213> ORGANISM: Artificial Sequence
<220> FEATURE:
<223> OTHER INFORMATION: synthesized peptide

<400> SEQUENCE: 13

Leu Leu Leu Leu Leu Leu Asp
1               5

<210> SEQ ID NO 14
<211> LENGTH: 8
<212> TYPE: PRT
<213> ORGANISM: Artificial Sequence
<220> FEATURE:
<223> OTHER INFORMATION: synthesized peptide

<400> SEQUENCE: 14

Leu Leu Leu Leu Leu Leu Asp Asp
1               5

<210> SEQ ID NO 15
<211> LENGTH: 7
<212> TYPE: PRT
<213> ORGANISM: Artificial Sequence
<220> FEATURE:
<223> OTHER INFORMATION: synthesized peptide

<400> SEQUENCE: 15

Leu Leu Leu Leu Leu Leu Lys
1               5

<210> SEQ ID NO 16
<211> LENGTH: 8
<212> TYPE: PRT
<213> ORGANISM: Artificial Sequence
<220> FEATURE:
<223> OTHER INFORMATION: synthesized peptide

<400> SEQUENCE: 16

Leu Leu Leu Leu Leu Leu Lys Lys
1               5

<210> SEQ ID NO 17
<211> LENGTH: 7
<212> TYPE: PRT
<213> ORGANISM: Artificial Sequence
<220> FEATURE:
<223> OTHER INFORMATION: synthesized peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MOD_RES
<222> LOCATION: (7)..(7)
<223> OTHER INFORMATION: AMIDATION
```

```
<400> SEQUENCE: 17

Ala Ala Ala Ala Ala Ala Lys
1               5
```